United States Patent [19]

Ryder et al.

[11] Patent Number: 4,637,919

[45] Date of Patent: Jan. 20, 1987

[54] LENS DISINFECTING APPLIANCE WITH IMPROVED VENTING FEATURE

[75] Inventors: Francis E. Ryder; Richard Rabenau, both of Arab, Ala.

[73] Assignee: Ryder International Corporation, Arab, Ala.

[21] Appl. No.: 668,293

[22] Filed: Nov. 5, 1984

[51] Int. Cl.$^4$ .............................................. A61L 2/18
[52] U.S. Cl. .................................. 422/300; 422/310; 55/385 C; 220/371
[58] Field of Search ..................... 55/182, 385 C, 159; 422/300, 301, 310; 220/371, 372; 206/5.1

[56] References Cited

U.S. PATENT DOCUMENTS

| | | | |
|---|---|---|---|
| 4,011,941 | 3/1977 | Parsons | 206/5.1 |
| 4,136,796 | 1/1979 | Dubois et al. | 220/371 |
| 4,197,097 | 4/1980 | Magorien et al. | 55/182 |
| 4,396,583 | 8/1983 | Le Boeuf | 422/116 |
| 4,512,771 | 4/1985 | Norton | 55/385 C |

*Primary Examiner*—David L. Lacey
*Attorney, Agent, or Firm*—Trexler, Bushnell & Wolters, Ltd.

[57] ABSTRACT

An appliance for disinfecting contact lenses utilizes a disinfecting solution, such as hydrogen peroxide, that liberates a gas during disinfecting action. The appliance has a container body with a removable cap that provides a sealed chamber except for a vent opening through the cap. A hydrophobic membrane filter is disposed across said vent opening and is substantially impermeable to the disinfecting solution but permeable to the liberated gas.

3 Claims, 7 Drawing Figures

LENS DISINFECTING APPLIANCE WITH IMPROVED VENTING FEATURE

BACKGROUND OF THE INVENTION

This invention relates to an improved appliance utilized for the chemical sterilization or disinfecting of small articles such as soft contact lenses.

In recent years, extremely soft contact lenses have been fabricated from a pliable plastic material that has the advantage of being able to be worn for extended periods of time without causing discomfort. These plastics are quite hydrophilic, and for that reason these contact lenses are susceptible to contamination by microorganisms. Consequently, the user must sterilize or disinfect the lenses, generally on a daily basis.

Various disinfecting techniques are now used in which the lenses are heated in a closed vessel in the presence of a saline solution, the heat being of such intensity and duration as to destroy the contaminating microorganism. More recently, a sterilizing process has been utilized that does not require heating. This process utilizes a bactericide, for example hydrogen peroxide, which oxidizes the bacteria on the lenses. In accordance with this process, the lenses are immersed for several hours in a weak solution of hydrogen peroxide, generally a 3% solution. Also within the solution is a platinum catalyst which hastens the decomposition of the hydrogen peroxide. If a bactericide such as hydrogen peroxide is used, care must be taken to insure that the solution is sufficiently neutralized or broken down so that the possibility of discomfort or injury to the eye of the user is precluded. Accordingly, the lenses are kept in the bactericide solution for a sufficient length of time to destroy all of the bacteria, following which the lenses are introduced into a rinsing solution to rinse out excess bactericide which may have a concentration that is unacceptably high.

Another problem encountered in the foregoing process is that there is a buildup of gas pressure within the sterilizing chamber which may tend to cause leaking and/or spillage, especially when the cap of the unit is not sealed properly. In this regard, when the hydrogen peroxide is brought into contact with the platinum catalyst, the hydrogen peroxide solution tends to break down into water, with oxygen being liberated. The liberated oxygen will cause a pressure build-up within the vessel that must be vented to the atmosphere. In U.S. Pat. No. 4,011,941, there is shown and described a contact lens sterilizer using hydrogen peroxide and in which the oxygen pressure is relieved through the expansion of a rubber O-ring. Thus, the O-ring normally seals the unit, but also functions as a check valve. However, when the valve is "open", there is still the possibility of solution leaking therethrough. Moreover, an O-ring can lose its resiliency over a period of time causing improper or ineffective valve operation. Additionally, the O-ring can become displaced leaving an opening through which bacteria from the ambience may enter the sterilizing chamber.

OBJECTS AND SUMMARY OF THE INVENTION

An object of this invention is to provide an appliance for disinfecting contact lenses or the like which employs a hydrophobic membrane filter that continuously vents the buildup of gas within the unit during the disinfecting process, while at the same time keeping the unit effectively sealed against leakage of disinfecting solution and the entrance of bacteria into the sterilizing chamber.

A further object of this invention is to provide an appliance of the type stated in which the disinfecting process can be carried out until the bactericide has been completely reduced which, in the case of hydrogen peroxide, results in liberation of sufficient oxygen to reduce the hydrogen peroxide to water.

It is also an object of this invention to provide an appliance of the type stated in which a single container may be used for both sterilization and rinsing of the lenses.

In accordance with the foregoing objects, the invention comprises an appliance for disinfecting contact lenses or the like wherein the lenses are disposed within the disinfecting solution which liberates the gas during the disinfecting action, said appliance comprising a container having a container body with an opening, a removable cap for closing said opening to form with said body a sealed chamber except for a vent opening for said chamber, a contact lens support attached to said cap and lying within the chamber when the cap is mounted on the body, and a hydrophobic membrane filter across said opening, said filter being substantially impermeable to the disinfecting solution but permeable to said gas.

In another aspect of the invention, the lens holder and cap are assembled such that an end flange of the holder is ultrasonically welded to the inside of the cap. The end flange and end wall of the cap are provided with aligned openings forming a vent from the sterilization chamber to the exterior of the unit. A separately fabricated tubular filter support with the membrane filter spanning the bore of the tube is press-fitted into the aligned openings of the end flange and cap such that the bore of the tubular filter support forms part of the vent. The foregoing eliminates the application of welding energy to the filter which may tend to close the gas permeable pores of the filter.

DETAILED DESCRIPTION

Figure 1:
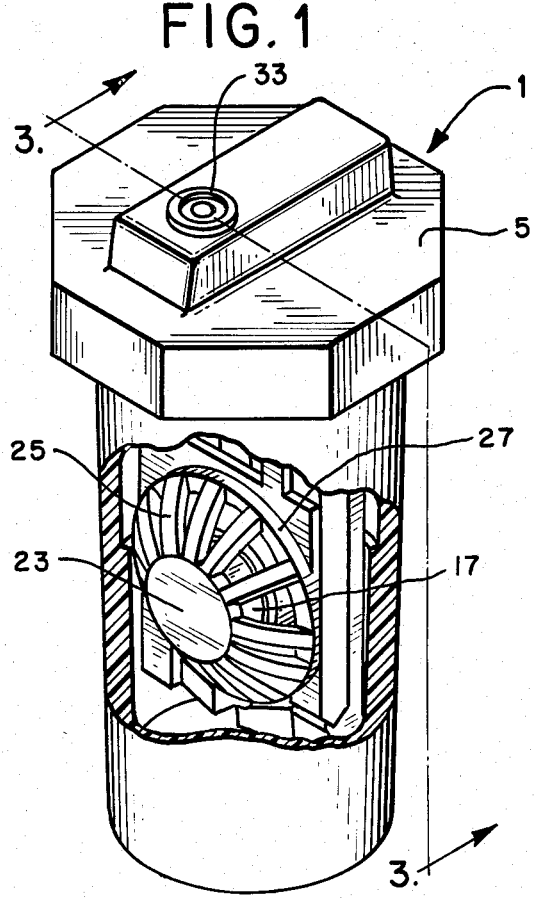
FIG. 1 is a perspective view, partially broken away in section, of a lens disinfecting appliance constructed in accordance with and embodying the present invention.
Figure 2:
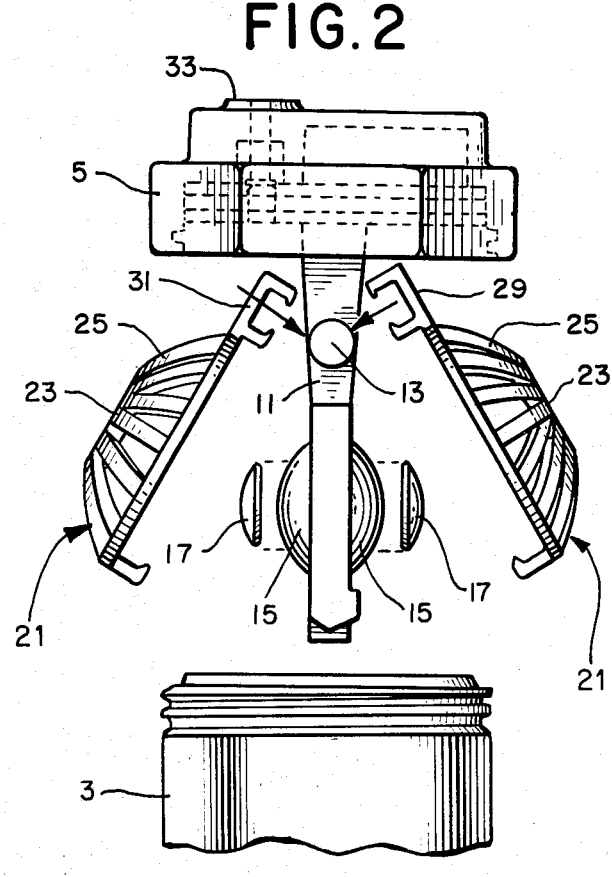
FIG. 2 is an exploded partial elevational view of the appliance.
Figure 3:
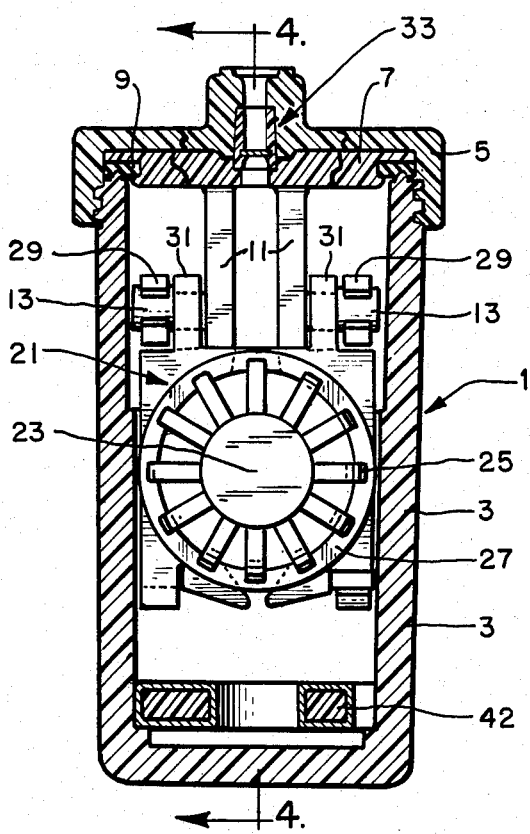
FIG. 3 is a sectional view taken along line 3—3 of FIG. 1.
Figure 4:
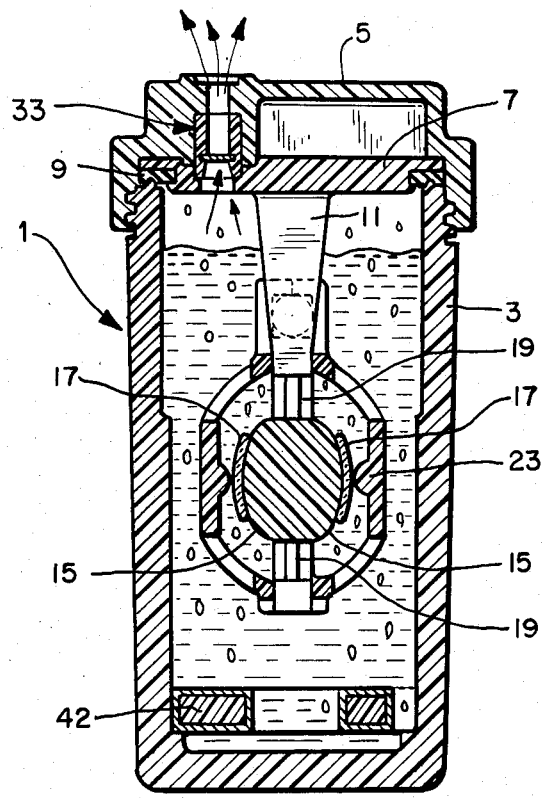
FIG. 4 is a sectional view taken along line 4—4 of FIG. 3.

Referring now in more detail and by reference characters to the drawings, which illustrates a preferred embodiment of the present invention, there is shown an appliance 1 comprising a container 3 with a generally cylindrical body having an end opening around which are formed threads for receiving a removable screw cap 5. The container 3 and the screw cap 5 are each formed of a suitable molded plastic material. Mounted in the screw cap 5 is a disc 7, the periphery of which includes a gasket 9 which seals against the rim of the container 3 at its opening. This forms a sealed container except at a vent opening, as will be presently more fully described.

The upper disc 7 forms part of a depending lens-supporting frame 11 which is integrally molded with the disc 7 and projects downwardly into the container 3 when the cap 5 is mounted thereon. Integrally molded on the frame 11 are opposed, axially aligned trunions or pins 13, 13, and below the pins 13, 13, is a button-like structure having opposed convex lens-receiving surfaces 15, 15. These surfaces 15, 15 receive the concave sides of the plastic contact lenses 17, 17. The button-like structure forming the convex lens-receiving surfaces 15, 15 is suspended from the remainder of the depending frame 11 by a series of ribs 19, permitting the passage of fluid through the frame 11.

Mounted on the pins 13, 13 are opposed lens covers 21, 21. Each lens cover has an end piece 23, 23 and a series of spokes 25, 25 radiating therefrom and being joined to respective rims 27, 27. At its upper end, each cover has a pair of fingers 29, 31 which snap-fit over the pins 13, 13 when the covers 21 are mounted onto the pins 13, 13. When so mounted, each cover swings independently of the other cover about the axis of the pins 13, 13. When in the fully-closed position, the covers 21, 21 retain the lenses 17, 17 on the lens supporting surfaces 15, 15.

Figure 5:
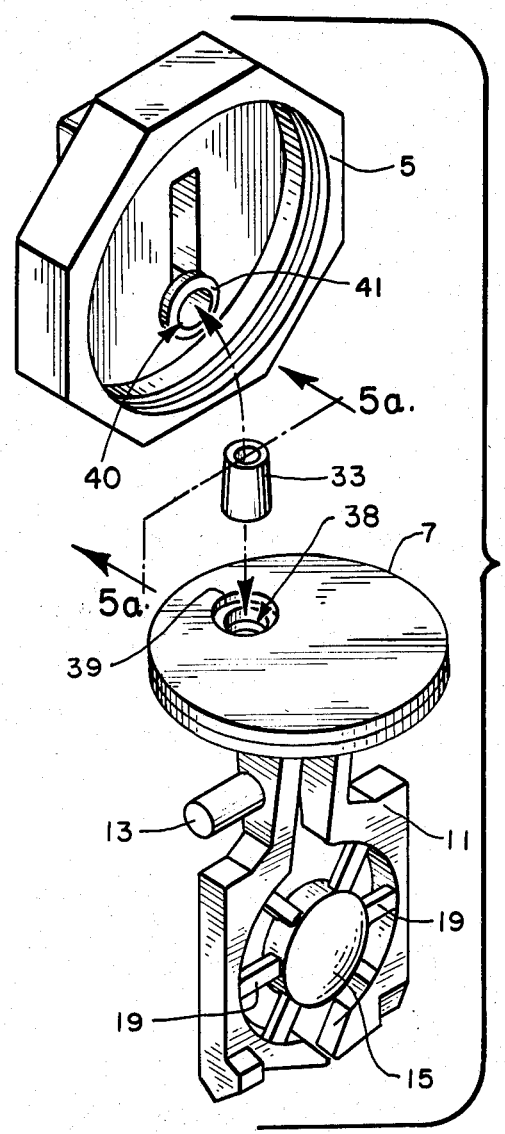
FIG. 5 is an exploded perspective view of the container cap and lens supporting frame in accordance with the present invention.
Figure 5A:
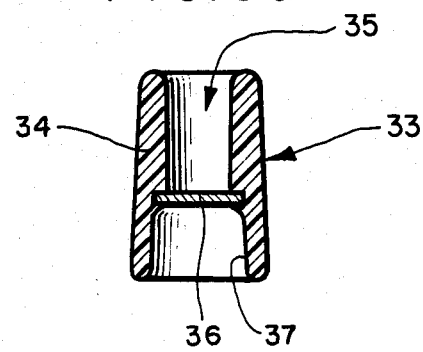
FIG. 5A is a sectional view, on an enlarged scale, taken along line 5A—5A of FIG. 5.

Affixed in the cap 5 is a hydrophobic membrane filter assembly 33 shown in a number of the figures and separately in FIG. 5A. This filter assembly comprises a tapered tubular member 34 having a bore 35. The bore 35 may have a larger diameter portion 37 at the larger diameter end of the tube 34. A filter medium 36 is carried by the tube 34 and is clinched throughout its entire periphery by the plastic of the tube 34 to provide a liquid-tight barrier across the bore of the tube. The filter medium is a membrane filter having pores which are sized at approximately 0.2 microns. Suffice it to say that the filter medium is an acrylic copolymer cast on a nylon non-woven substrate. The material is available commercially from Millipore Corporation, Concord, Mass. The structure in FIG. 5A is molded as an individual piece with the filter medium therein prior to assembly with the cap 5.

Figure 6:
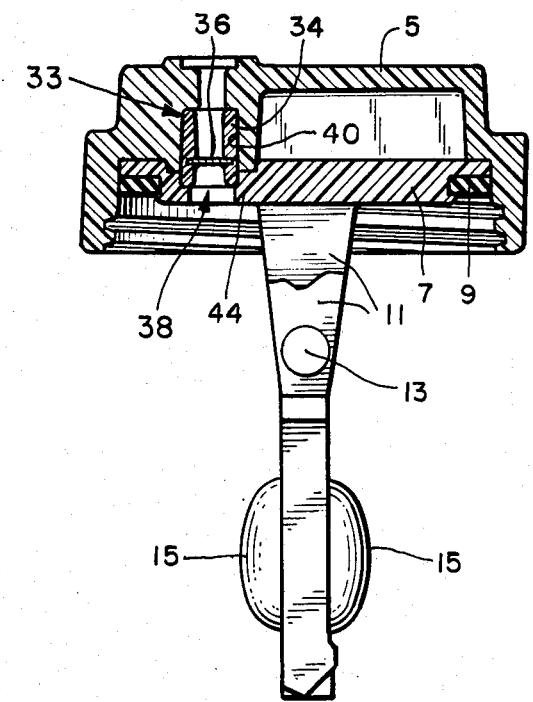
FIG. 6 is a partial sectional view of the assembled container cap and lens supporting frame of the present invention.

In assembly of the appliance, the upper disc 7 with attached depending frame 11 is fabricated separately from the cap 5. The cap 5 is provided with a bore 40 surrounded by a boss 41, FIG. 5, which bore 40 is slightly tapered. As best seen in FIG. 5, the upper disc 7 is formed with a bore 38 having a counterbore 39 to accommodate the boss 41. Upon assembly, the disc 7 is initially disposed within the cap 5, and the bore 38 is placed in alignment with bore 40 in the cap proper. The boss 41 and counterbore 39 cooperate to facilitate proper initial alignment. Thereafter, the periphery of the disc 7 is ultrasonically weld the cap. After welding, the filter assembly 33 is into the aligned holes 38, 40 such that the bore of the tubular filter support forms part of the vent and with the opening across the vent being obstructed only by the filter medium 36. The respective tapers on the tubular member 34 and bore 40 serve to provide a widge type seal that prevents the entry of contaminants. Also it should be noted that end of the bore 38 opposite the counterbore 39 has a reduced diameter portion 44 of an inner diameter less than the outer diameter of the larger diameter end of the tube member 34, which difference is exaggerated slightly in FIG. 6. Thus, upon insertion of the filter assembly 33, the larger diameter end of member 34 will be received within the bore 38 with a snap-type fit, the larger diameter end of member 34 snapping past the reduced diameter end portion 44 to effect a positive retention of the filter assembly 33 within the aligned bores 40 and 38.

The structure which permits insertion of the filter assembly 33 after welding of the disc 7 to the cap 5 is an important feature. Should the filter assembly be assembled prior to the ultrasonic welding of the disc 7 and cap 5, there is a danger that the ultrasonic waves will damage, if not destroy, the hydrophobic membrane 36.

In use, the soft contact lenses 17 are placed within the lens support and are held in place by the covers 21. Hydrogen peroxide sterilizing solution is then poured into the open end of the container 3, and in addition, a catalyst 42 may then be introduced into the solution. Alternately, the catalyst, which is disclosed in said earlier mentioned U.S. Pat. No. 4,011,941 may be disposed within container 3 prior to introduction of the sterilizing solution. This catalyst comprises a catalytic reactor member with the preferred catalytic material being a very thin layer of platinum black which has been deposited on a molded substrate of the desired shape. As the reaction proceeds, the oxygen liberated upon decomposition of the hydrogen peroxide will be vented through the 0.2 micron membrane 36, but the liquid will not leak therethrough. Further, the 0.2 micron membrane also will prevent any bacteria or contaminants from entering the lens case 1.

We claim:
1. An appliance for disinfecting contact lenses or the like wherein said lenses are disposed within a disinfecting solution capable of being decomposed to cause a gas to be liberated, said appliance comprising: a container having a body with an open end; a cap assembly closing said container open end; lens holder means for supporting a pair of contact lenses being disposed within said container body; said cap assembly comprising an outer cap member and a disc member assembled in surface-to-surface abutting engagement, aligned openings formed in said outer cap member and said disc member defining a vent passageway for venting liberated gases from said appliance, an inner portion of an opening in said outer cap member and an outer portion of the opening in said disc member, each including a counter bore, which counter bores are adjacent to each other and define a chamber which is intermediate the ends of said vent passageway and bridges between the cap and disc members, a filter assembly disposed in said chamber and bridging between said outer cap and said disc member, said filter assembly including a tubular support member defining an inner bore and formed from a molded plastic material, a filter membrane formed from a gas permeable hydrophobic material supported by said tubular member as an integral component thereof, said membrane being insert molded with said tubular support member and disposed within said inner bore, said tubular support member having an outer diameter sized with respect to the diameter of said chamber, such that said filter assembly is press fitted within said chamber.

2. An appliance according to claim 1 wherein the vent passageway includes an inner portion having an inner diameter less than the outer diameter of said tubular support member such that said press fit is a snap fit.

3. An appliance according to claim 1, wherein said cap member and said disc member are ultrasonically welded together and said filter assembly is disposed within said chamber by a snap fit type engagement.

* * * * *